United States Patent
Narimatsu

(10) Patent No.: US 6,740,043 B2
(45) Date of Patent: May 25, 2004

(54) PRESSURE-PULSE-WAVE DETECTING APPARATUS

(75) Inventor: Kiyoyuki Narimatsu, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 226 days.

(21) Appl. No.: 10/014,529

(22) Filed: Dec. 14, 2001

(65) Prior Publication Data

US 2002/0173726 A1 Nov. 21, 2002

(30) Foreign Application Priority Data

May 16, 2001 (JP) .......................... 2001-146648

(51) Int. Cl.[7] .............................................. A61B 5/00
(52) U.S. Cl. ........................ 600/485; 600/500; 600/494; 600/490
(58) Field of Search ................................ 600/485, 490, 600/493–6, 500

(56) References Cited

U.S. PATENT DOCUMENTS

| | | | |
|---|---|---|---|
| 5,261,412 A | * 11/1993 | Butterfield et al. | 600/485 |
| 5,273,046 A | * 12/1993 | Butterfield et al. | 600/485 |
| 5,497,779 A | *  3/1996 | Takaya et al. | 600/485 |
| 6,290,650 B1 | *  9/2001 | Butterfield et al. | 600/485 |
| 6,428,482 B1 | *  8/2002 | Sunagawa et al. | 600/485 |
| 6,475,155 B2 | * 11/2002 | Ogura et al. | 600/500 |
| 6,610,017 B2 | *  8/2003 | Oka | 600/485 |

FOREIGN PATENT DOCUMENTS

JP            11-9562 A       1/1999

\* cited by examiner

Primary Examiner—Robert L. Nasser

(57) ABSTRACT

An apparatus for detecting a pressure pulse wave produced by an artery of a living subject, including a pressure-pulse-wave sensor which has a pressing surface, and pressure-detecting elements that are arranged, in the pressing surface, in an array in a widthwise direction of the artery, a pressing device which presses, with a pressing force, the pressure-pulse-wave sensor against the artery via a skin of the subject, so that each of the pressure-detecting elements detects the pressure pulse wave produced by the artery, a highest-pressure-detecting-element selecting device for selecting, as a highest-pressure-detecting element, a first one of the pressure-detecting elements that detects a highest one of respective pressures corresponding to the respective pressure pulse waves detected by the pressure-detecting elements, and a pressing-force checking device for judging whether the pressing force of the pressing device applied to the pressure-pulse-wave sensor is appropriate, based on a time difference between a time when a prescribed portion of the pressure pulse wave is detected by the highest-pressure-detecting element and a time when the prescribed portion of the pressure pulse wave is detected by a second one of the pressure-detecting elements that is distant by a prescribed distance from the highest-pressure-detecting element in a direction toward one of opposite ends of the array of pressure-detecting elements.

6 Claims, 14 Drawing Sheets

PRESSURE-PULSE-WAVE DETECTING APPARATUS

BACKGROUND OF THE INVENTION

1. Field of the Invention

The present invention relates to a pressure-pulse-wave detecting apparatus which presses an artery of a living subject and detects a pressure pulse wave produced from the artery.

2. Related Art Statement

A pressure-pulse-wave detecting apparatus which includes a pressure-pulse-wave sensor, presses the sensor against an artery of a living subject via skin, and detects a pressure pulse wave produced from the artery, is employed in, e.g., a blood-pressure monitoring apparatus which successively determines blood-pressure values of the subject based on the pressure pulse wave, or a pulse-wave-propagation-velocity measuring apparatus which measures a pulse-wave propagation velocity based on at least the pressure pulse wave.

In the above-mentioned pressure-pulse-wave detecting apparatus, a magnitude of the pressure pulse wave detected by the pressure-pulse-wave sensor largely depends on a pressing force applied to the sensor, and additionally a phase of the pressure pulse wave more or less depends on the pressing force. Therefore, the pressure-pulse-wave detecting apparatus needs to press the artery with a pressing force (hereinafter, this pressing force will be referred to as an "optimum" pressing force) which assures that a portion of the wall of the artery is flattened. Meanwhile, usually, the pressure-pulse-wave sensor has a plurality of pressure-detecting elements that are arranged in an array in a widthwise direction of the artery, so that even if the sensor is more or less moved relative to the artery, at least one of the pressure-detecting elements remains positioned right above the artery to be able to detect the pressure pulse wave.

A method of determining the above-mentioned optimum pressing force is disclosed in, e.g., Japanese Patent Document No. 11-9562. This document discloses a blood-pressure monitoring apparatus including the above-explained pressure-pulse-wave detecting apparatus, and teaches that the pressure-pulse-wave sensor is worn on a wrist to detect a pressure pulse wave produced by a radial artery. According to this document, the optimum pressing force applied to the pressure-pulse-wave sensor is determined as follows: First, the pressing force applied to the sensor is continuously increased up to a value at which the entirety of the wall of the radial artery is flattened. Then, one of the pressure-detecting elements that detects, during the continuous increasing of the pressing force, the highest pressure of the respective pressures detected by all the elements is selected (as a highest-pressure detecting element), and a pressing force at which the pressure pulse wave detected by the selected element exhibits a maximal amplitude, or a pressing force that falls within a range whose center is equal to that pressing force, is determined as the optimum pressing force.

In the case where a pressure-pulse-wave sensor of, e.g., the pressure-pulse-wave detecting apparatus disclosed in the above-mentioned document, is worn on a wrist to detect a pressure pulse wave from a radial artery, the radial artery is sandwiched between the sensor and a radius. Therefore, as the pressing force applied to the sensor is increased, the radial artery can be substantially completely flattened. That is, since the radial artery is supported on the radius, the artery can be completely flattened. However, there are many arteries that are not supported on such bones. That is, if the pressing force applied to the sensor pressing an artery not supported on a bone is continuously increased, the artery cannot be completely flattened. Thus, in that case, an appropriate pressing force which causes only a portion of the wall of the artery to be flattened may not be determined.

SUMMARY OF THE INVENTION

It is therefore an object of the present invention to provide a pressure-pulse-wave detecting apparatus which can determine an appropriate pressing force that causes only a portion of a wall of an artery to be flattened, without needing to flatten an entirety of the wall of the artery.

The Inventor has carried out extensive studies to achieve the above object, and has found that in a state in which the pressing force applied to the pressure-pulse-wave sensor causes a portion of a wall of an artery to be flattened, there is no phase difference between respective pressure pulse waves detected by respective pressure-detecting elements of the sensor that are positioned right above the flattened portion of the arterial wall, but there is a phase delay of a pressure pulse wave detected by a pressure-detecting element positioned right above a non-flattened portion of the arterial wall, from the phase of the pressure pulse waves detected by pressure-detecting elements positioned right above the flattened portion, owing to a visco-elasticity of the non-flattened portion. Thus, if a phase of a pressure pulse wave detected by a pressure-detecting element distant by a prescribed distance from the highest-pressure detecting element in a direction toward an end of the array of pressure-detecting elements, e.g., an pressure-detecting element next to the highest-pressure detecting element, is not delayed from the phase of the pressure pulse wave detected by the highest-pressure detecting element, or if the former phase is later than the latter phase by a short time only, it can be judged that a portion of the wall of the artery is flattened.

In addition, the Inventor has found that there is substantially no pulse-pressure difference between the respective pressure pulse waves detected by the respective pressure-detecting elements positioned right above the flattened portion of the arterial wall, but a pulse pressure of the pressure pulse wave detected by the pressure-detecting element positioned right above the non-flattened portion of the arterial wall is smaller than the pulse pressures of the pressure pulse waves detected by pressure-detecting elements positioned right above the flattened portion, owing to a pressure loss caused by the visco-elasticity of the non-flattened portion. Thus, if a pulse pressure of the pressure pulse wave detected by the pressure-detecting element distant by the prescribed distance from the highest-pressure detecting element in the direction toward the end of the array of pressure-detecting elements, is substantially equal to the pulse pressure of the pressure pulse wave detected by the highest-pressure detecting element, it can be judged that a portion of the wall of the artery is flattened. The present invention has been developed based on these findings.

The above object has been achieved by the present invention. According to a first aspect of the present invention, there is provided an apparatus for detecting a pressure pulse wave produced by an artery of a living subject, comprising a pressure-pulse-wave sensor which has a pressing surface, and a plurality of pressure-detecting elements that are arranged, in the pressing surface, in an array in a widthwise direction of the artery; a pressing device which presses, with a pressing force, the pressure-pulsewave sensor against the artery via a skin of the subject, so that each of the pressure-detecting elements detects the pressure pulse wave produced by the artery; a highest-pressure-detecting-element selecting means for selecting, as a highest-pressure-detecting element, a first one of the pressure-detecting elements that detects a highest one of respective pressures corresponding to the respective pressure pulse waves detected by the pressure-detecting elements; and a pressing-force checking means for judging whether the pressing force of the pressing device applied to the pressure-pulse-wave sensor is appropriate, based on a time difference between a first time when a prescribed portion of the pressure pulse wave is detected by the highest-pressure-detecting element and a second time when the prescribed portion of the pressure pulse wave is detected by a second one of the pressure-detecting elements that is distant by a prescribed distance from the highest-pressure-detecting element in a direction toward one of opposite ends of the array of pressure-detecting elements.

According to this aspect, the pressing-force checking means judges whether the pressing force applied to the pressure-pulse-wave sensor is appropriate, based on the time difference between the time when the prescribed portion of the pressure pulse wave is detected by the highest-pressure-detecting element and the time when the prescribed portion of the pressure pulse wave is detected by the pressure-detecting element distant by the prescribed distance from the highest-pressure-detecting element in the direction toward one end of the array of pressure-detecting elements. Thus, the present apparatus can determine an appropriate pressing force that causes a portion of the wall of the artery to be flattened, without needing to substantially completely flatten the arterial wall.

According to a second aspect of the present invention, there is provided an apparatus for detecting a pressure pulse wave produced by an artery of a first portion of a living subject, comprising a pressure-pulse-wave sensor which has a pressing surface, and a plurality of pressure-detecting elements that are arranged, in the pressing surface, in an array in a widthwise direction of the artery; a pressing device which presses, with a pressing force, the pressure-pulse-wave sensor against the artery via a skin of the subject, so that each of the pressure-detecting elements detects the pressure pulse wave produced by the artery of the first portion; a heartbeat-synchronous-signal detecting device which detects a heartbeat-synchronous signal produced from a second portion of the subject that is different from the first portion; a highest-pressure-detecting-element selecting means for selecting, as a highest-pressure-detecting element, a first one of the pressure-detecting elements that detects a highest one of respective pressures corresponding to the respective pressure pulse waves detected by the pressure-detecting elements; a standard-pulse-wave-propagation-velocity-related-information obtaining means for obtaining, as a piece of standard pulse-wave-propagation-velocity-related information, a first piece of pulse-wave-propagation-velocity-related information that is related to a velocity at which the pressure pulse wave propagates between the first and second portions of the subject, based on a first time difference between a first time when a prescribed portion of the pressure pulse wave is detected by the highest-pressure-detecting element and a second time when a corresponding prescribed portion of the heartbeat-synchronous signal is detected by the heartbeat-synchronous-signal detecting device; a comparison-pulse-wave-propagation-velocity-related-information obtaining means for obtaining, as a piece of comparison pulse-wave-propagation-velocity-related information, a second piece of pulse-wave-propagation-velocity-related information that is related to the velocity at which the pressure pulse wave propagates between the first and second portions of the subject, based on a second time difference between a third time when the prescribed portion of the pressure pulse wave is detected by a second one of the pressure-detecting elements that is distant by a prescribed distance from the highest-pressure-detecting element in a direction toward one of opposite ends of the array of pressure-detecting elements, and the second time when the corresponding prescribed portion of the heartbeat-synchronous signal is detected by the heartbeat-synchronous-signal detecting device; and a pressing-force checking means for judging whether the pressing force of the pressing device applied to the pressure-pulse-wave sensor is appropriate, based on a comparison value obtained by comparing the piece of standard pulse-wave-propagation-velocity-related information and the piece of comparison pulse-wave-propagation-velocity-related information with each other.

According to this aspect, the standard-pulse-wave-propagation-velocity-related-information obtaining means obtains the piece of standard pulse-wave-propagation-velocity-related information based on the pressure pulse wave detected by the highest-pressure-detecting element and the heartbeat-synchronous signal detected by the heartbeat-synchronous signal detecting device, and the comparison-pulse-wave-propagation-velocity-related-information obtaining means obtains the piece of comparison pulse-wave-propagation-velocity-related information based on the pressure pulse wave detected by the pressure-detecting element distant by the prescribed distance from the highest-pressure-detecting element in the direction toward one end of the array of pressure-detecting elements and the heartbeat-synchronous signal detected by the heartbeat-synchronous-signal detecting device. Since both the piece of standard pulse-wave-propagation-velocity-related information and the piece of comparison pulse-wave-propagation-velocity-related information are obtained based on the prescribed portion of the heartbeat-synchronous signal, as one of two reference points, a difference between the two pieces of information is caused by a time difference between the time when the prescribed portion of the pressure pulse wave is detected by the highest-pressure-detecting element and the time when the prescribed portion of the pressure pulse wave is detected by the pressure-detecting element distant by the prescribed distance from the highest-pressure-detecting element. Therefore, the pressing-force checking means can judge whether the pressing force applied to the pressure-pulse-wave sensor is appropriate, based on the comparison value obtained by comparing the two pieces of information with each other. Thus, the present apparatus can determine an appropriate pressing force that causes a portion of the wall of the artery to be flattened, without needing to substantially completely flatten the arterial wall.

According to a third aspect of the present invention, there is provided an apparatus for detecting a pressure pulse wave produced by an artery of a living subject, comprising a pressure-pulse-wave sensor which has a pressing surface, and a plurality of pressure-detecting elements that are arranged, in the pressing surface, in an array in a widthwise direction of the artery; a pressing device which presses, with a pressing force, the pressure-pulse-wave sensor against the artery via a skin of the subject, so that each of the pressure-detecting elements detects the pressure pulse wave produced by the artery; a highest-pressure-detecting-element selecting means for selecting, as a highest-pressure-detecting element, a first one of the pressure-detecting elements that detects a highest one of respective pressures corresponding to the respective pressure pulse waves detected by the pressure-detecting elements; a standard-pulse-pressure determining means for determining, as a standard pulse pressure, a pulse pressure of the pressure pulse wave detected by the highest-pressure-detecting element; a comparison-pulse-pressure determining means for determining, as a comparison pulse pressure, a pulse pressure of the pressure pulse wave detected by a second one of the pressure-detecting elements that is distant by a prescribed distance from the highest-pressure-detecting element in a direction toward one of opposite ends of the array of pressure-detecting elements; and a pressing-force checking means for judging whether the pressing force of the pressing device applied to the pressure-pulse-wave sensor is appropriate, based on a comparison value obtained by comparing the standard pulse pressure and the comparison pulse pressure with each other.

According to this aspect, the standard-pulse-pressure determining means determines, as the standard pulse pressure, the pulse pressure of the pressure pulse wave detected by the highest-pressure-detecting element, and the comparison-pulse-pressure determining means determines, as the comparison pulse pressure, the pulse pressure of the pressure pulse wave detected by the pressure-detecting element distant by the prescribed distance from the highest-pressure-detecting element in the direction toward one end of the array of pressure-detecting elements. Since a fact that the standard pulse pressure and the comparison pulse pressure are substantially equal to each other indicates that a portion of the wall of the artery is flattened, the pressing-force checking means can judge whether the pressing force applied to the pressure-pulse-wave sensor is appropriate, based on the comparison value obtained by comparing the standard pulse pressure and the comparison pulse pressure with each other. Thus, the present apparatus can determine an appropriate pressing force that causes a portion of the wall of the artery to be flattened, without needing to substantially completely flatten the arterial wall.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Hereinafter, there will be described an embodiment of the present invention in detail by reference to the drawings.

Figure 1:
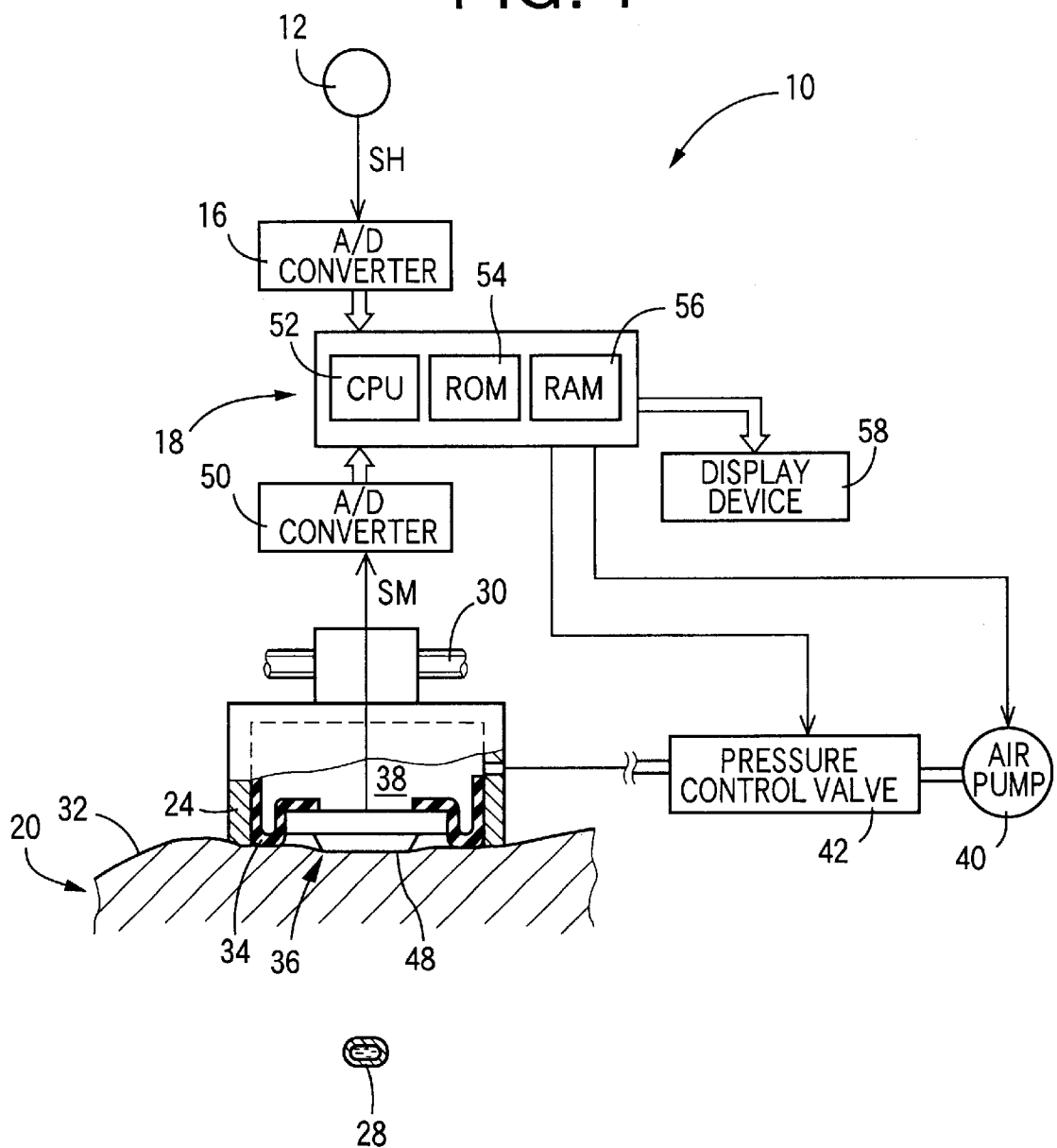
FIG. 1 is a diagrammatic view of a construction of a pulse-wave-propagation-velocity measuring apparatus functioning as a pressure-pulse-wave detecting apparatus, to which the present invention is applied.

FIG. 1 shows a diagrammatic view of a construction of a pulse-wave-propagation-velocity measuring apparatus 10 functioning as a pressure-pulse-wave detecting apparatus, to which the present invention is applied. The pulse-wave-propagation-velocity measuring apparatus 10 includes a heart-sound microphone 12, and a pressure-pulse-wave detecting probe 14 which is illustrated in detail in FIG. 2. The heart-sound microphone 12 is worn on a prescribed location on a body surface of a chest of a living subject, detects heart sounds produced by the heart of the subject, and generates a heart-sound signal SH representing the detected heart sounds. The heart-sound signal SH generated by the heart-sound microphone 12 is supplied to a control device 18 via an A/D (analog-to-digital) converter 16. Since the heart sounds represented by the heart-sound signal SH are a heartbeat-synchronous signal that is produced in synchronism with the heartbeat of the subject, the heart-sound microphone 12 functions as a heartbeat-synchronous-signal detecting device.

Figure 2:
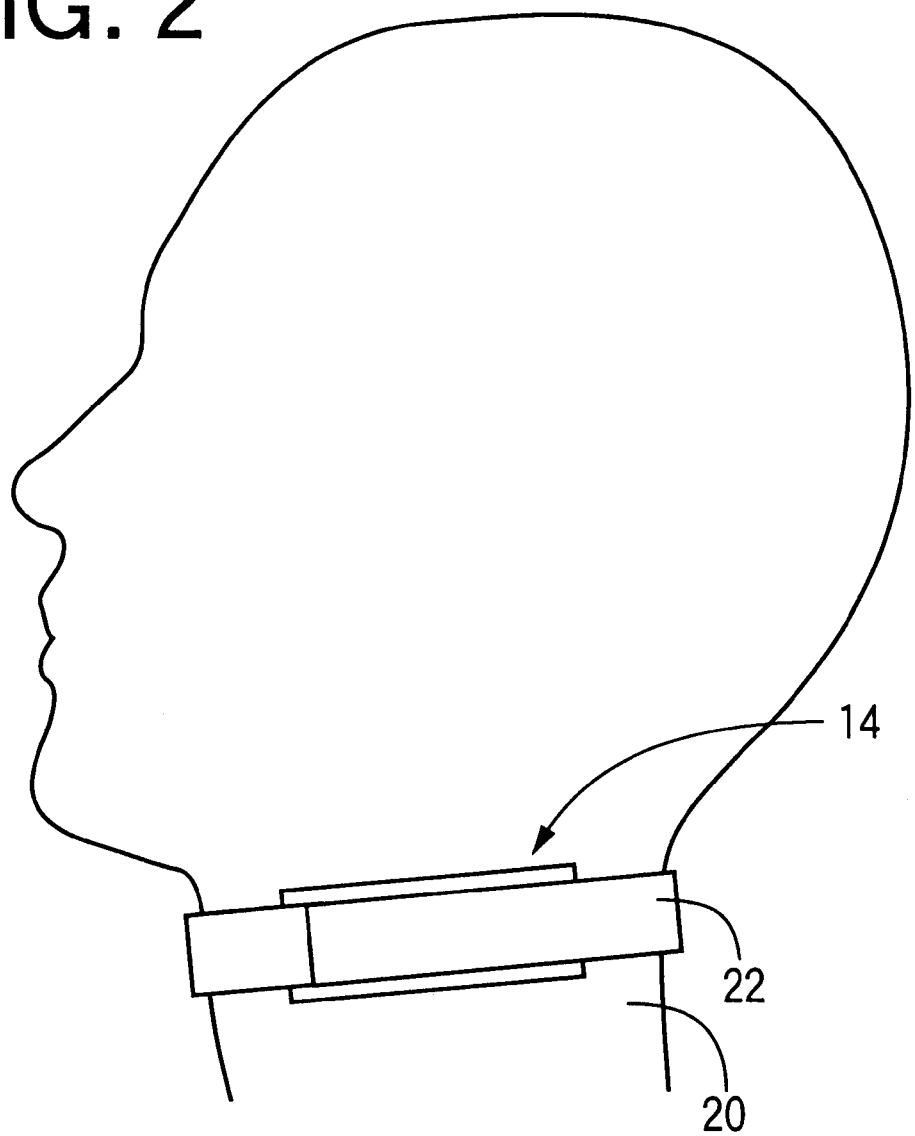
FIG. 2 is a view showing a state in which a pressure-pulse-wave detecting probe of the pulse-wave-propagation-velocity measuring apparatus of FIG. 1 is worn on a neck of a patient.
Figure 3:
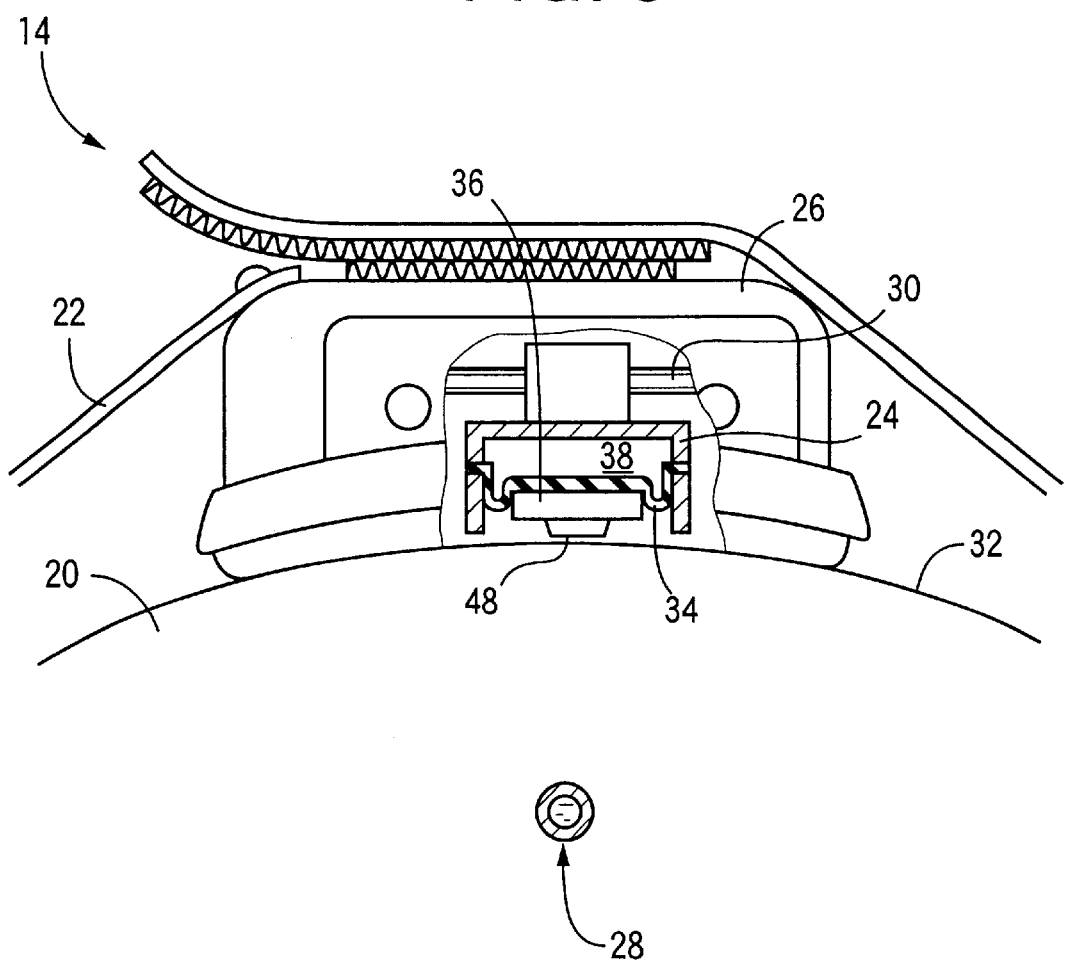
FIG. 3 is an enlarged view of the pressure-pulse-wave detecting probe of FIG. 1, a portion of the probe being cut away.

The pressure-pulse-wave detecting probe 14 is worn on a neck 20 of a patient, as illustrated in FIG. 2, with the help of a fastening band 22. As shown in detail in FIG. 3, the pressure-pulse-wave detecting probe 14 includes a container-like sensor housing 24; a case 26 which accommodates the sensor housing 24; and a feed screw 30 which is threadedly engaged with the sensor housing 24 and is rotated by an electric motor, not shown, provided in the case 26 so as to move the sensor housing 24 in a widthwise direction of a carotid artery 28. With the help of the fastening band 22, the pressure-pulse-wave detecting probe 14 is detachably attached to the neck 20, such that an open end of the sensor housing 24 is opposed to a body surface 32 of the neck 20.

In addition, the pressure-pulse-wave detecting probe 14 includes a pressure-pulse-wave sensor 36 which is secured via a diaphragm 34 to an inner wall of the sensor housing 24, such that the sensor 36 is movable relative to the housing 24 and is advanceable out of the open end of the same 24. The sensor housing 24, the diaphragm 34, etc. cooperate with one another to define a pressure chamber 38, which is supplied with a pressurized air from an air pump 40 via a pressure-control valve 42, as shown in FIG. 1, so that the pressure-pulse-wave sensor 36 is pressed against the body surface 32 with a pressing force corresponding to the air pressure (Pa) in the pressure chamber 38. Thus, the pressing force applied to the sensor 36 is expressed in terms of the air pressure (mmHg) in the pressure chamber 38.

The sensor housing 24 and the diaphragm 34 cooperate with each other to provide a pressing device 44 which presses the pressure-pulse-wave sensor 36 against the carotid artery 28, and the feed screw 30 and the not-shown motor cooperate with each other to provide a widthwise-direction moving device 46 which moves the pressure-pulse-wave sensor 36 in the widthwise direction of the carotid artery 28 and thereby changes a pressing position where the sensor 36 is pressed on the body surface 32.

Figure 4:
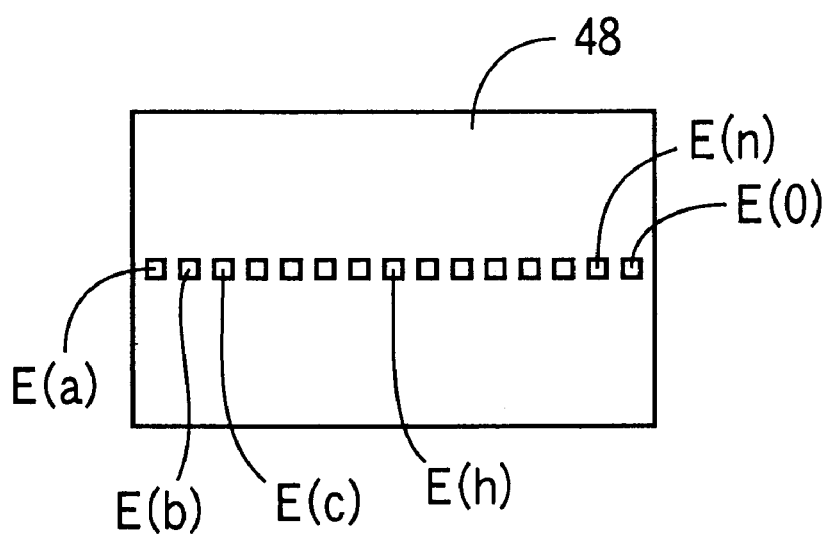
FIG. 4 is a view for explaining a state in which an array of pressure-sensing elements is provided in a pressing surface of a pressure-pulse-wave sensor of the probe of FIG. 1.

The pressure-pulse-wave sensor 36 has a pressing surface 48, and a plurality of semiconductor pressure-sensing elements (i.e., pressure-detecting elements) E which are arranged in the pressing surface 48 at a regular interval in the widthwise direction of the carotid artery 28, i.e., in the direction of movement of the sensor 36 parallel to the feed screw 30, over a length greater than the diameter of the carotid artery 28. For example, as shown in FIG. 4, fifteen semiconductor pressure-sensing elements E(a), E(b), . . . , E(o) are arranged at a regular interval of 0.6 mm.

The pressure-pulse-wave detecting probe 14, constructed as described above, is pressed against the body surface 32 of the neck 20 right above the carotid artery 28, so as to detect a pressure pulse wave, i.e., an oscillatory pressure wave which is produced from the carotid artery 28 and is propagated to the body surface 32, and supplies a pressure-pulse-wave signal SM representing the detected pressure pulse wave, to the control device 18 via an A/D converter 50.

The control device 18 is provided by a so-called microcomputer including a central processing unit (CPU) 52, a read only memory (ROM) 54, a random access memory (RAM) 56 and an input-and-output (I/O) port, not shown. The CPU 52 processes signals according to the control programs pre-stored in the ROM 54 by utilizing the temporary-storage function of the RAM 56. In addition, the CPU 52 supplies drive signals via the I/O port to respective drive circuits, not shown, associated with the pressure control valve 42 and the air pump 40 so as to control the pressure in the pressure chamber 38 to an optimum pressing force HDPO. Moreover, the CPU 52 determines a pulse-wave propagation velocity PWV based on the heart-sound SH signal supplied from the heart-sound microphone 12 and the pressure-pulse-wave signal SM supplied from the pressure-pulse-wave sensor 36, and operates a display device 58 to display the thus determined pulse-wave propagation velocity PWV.

Figure 6:
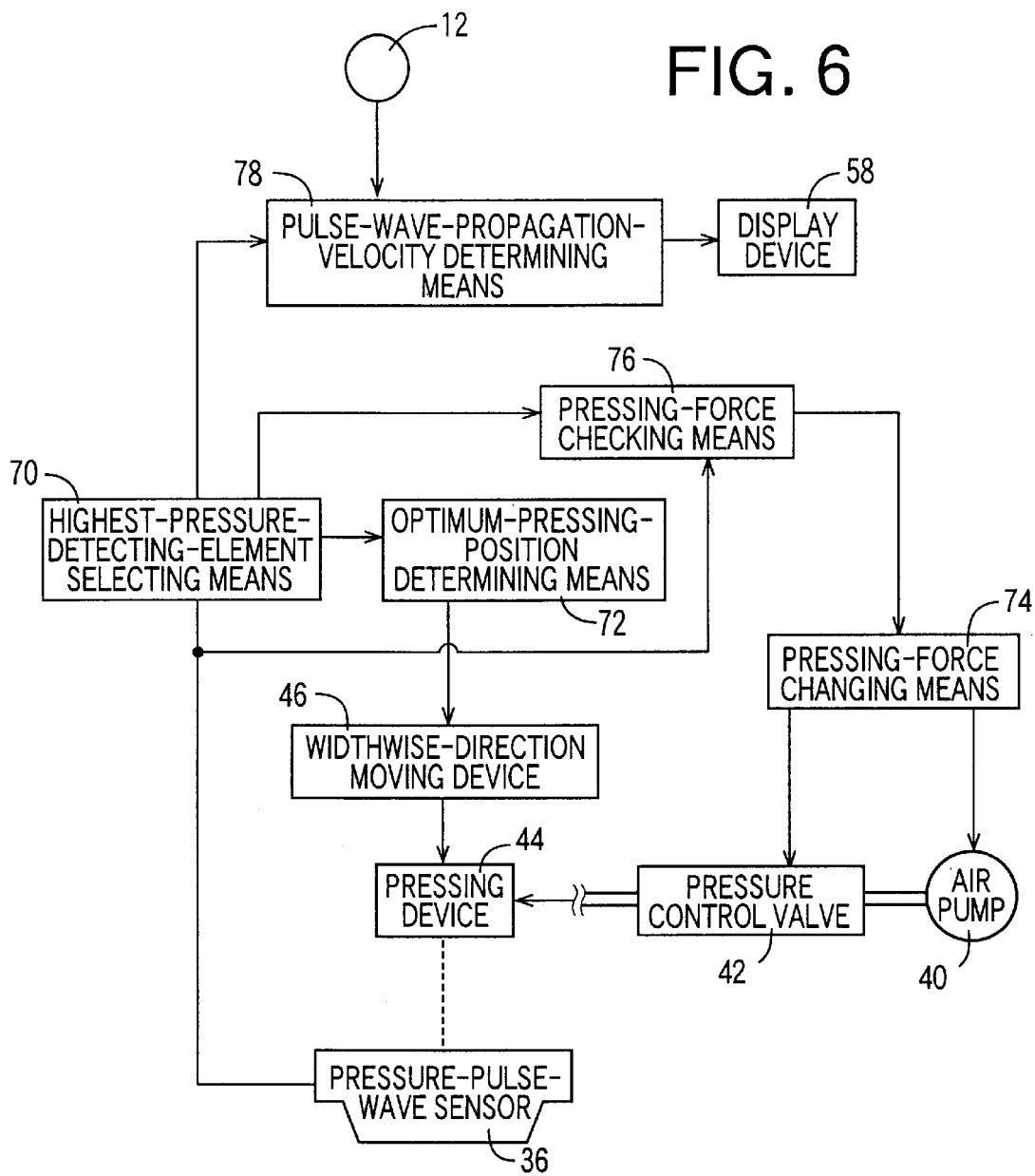
FIG. 6 is a block diagram for explaining essential functions of a control device of the pulse-wave-propagation-velocity measuring apparatus of FIG. 1.

FIG. 6 is a block diagram for explaining essential control functions of the control device 18 of the pulse-wave-propagation-velocity measuring apparatus 10. In FIG. 6, a highest-pressure-detecting-element selecting means 70 selects, as a highest-pressure detecting element EM, one of the semiconductor pressure-sensing elements E of the pressure-pulse-wave sensor 36 that detects the highest pressure of the respective pressures detected by all the elements E. More specifically described, the selecting means 70 determines one of the respective pressure pulse waves detected by the pressure-sensing elements E that has the highest peak point of respective peak points of the detected pressure pulse waves and selects, as the highest-pressure detecting element EM, one of the pressure-sensing elements E that detects the pressure pulse wave having the highest peak point. The highest-pressure detecting element EM is one of the pressure-sensing elements E that is positioned right above the carotid artery 28.

An optimum-pressing-position determining means 72 judges, for example, when the pressure-pulse-wave sensor 36 is initially worn on the patient, whether a prescribed pressing-position changing condition is satisfied, i.e., whether the highest-pressure detecting element EM is positioned in one of prescribed opposite end portions of the array of pressure-sensing elements E. Each of the prescribed opposite end portions of the array of elements E may be a range having a prescribed length including a corresponding one of the opposite ends of the array of elements E, or a range accommodating a prescribed number of elements E including a corresponding one of the respective elements E located at the opposite ends of the array. When this pressing-position changing condition is satisfied, the optimum-pressing-position determining means 72 carries out the following pressing-position changing operation: After the pressing device 44 once moves the pressure-pulse-wave sensor 36 away from the body surface 32, the widthwise-direction moving device 46 moves the pressing device 44 and the sensor 36 over a prescribed distance, and then the pressing device 44 again presses the sensor 36 with a prescribed, considerably low pressing force HDP1. In this state, the determining means 72 judges again whether the prescribed pressing-position changing condition is satisfied. The determining means 72 repeats carrying out the above-described operation and judgment till the pressing-position changing condition is not satisfied any longer, preferably till the highest-pressure detect element EM is positioned in a prescribed middle portion of the array of elements E. The length, or element number, employed for each of the opposite end portions of the array of elements E is prescribed based on the diameter of the artery (i.e., the carotid artery 28) to be pressed by the pressure-pulse-wave sensor 36, and may be one fourth of the diameter.

A pressing-force changing means 74 changes, after the optimum-pressing-position determining means 72 positions the pressure-pulse-wave sensor 36 at the optimum pressing position, a pressing force HDP (i.e., hold-down pressure) applied by the pressing device 44 to the sensor 36, within a prescribed pressing-force range, either stepwise in response to each heartbeat of the patient or continuously at a prescribed, considerably low rate. When a pressing-force checking means 76, described below, judges that a current pressing force HDP being applied to the sensor 36 is appropriate, during the changing of the pressing force HDP, the changing means 74 determines the current pressing force HDP as an optimum pressing force HDPO and maintains the pressing force applied to the sensor 36 at the thus determined optimum pressing force HDPO.

The pressing-force checking means 76 judges whether the pressing force HDP applied to the pressure-pulse-wave sensor 36 is appropriate, based on a pressure pulse wave detected by the highest-pressure detecting element EM selected by the highest-pressure-element selecting means 70, and a pressure pulse wave detected by another semiconductor pressure-sensing element E (hereinafter, referred to as the "comparison" element EC) distant by a prescribed distance from the highest-pressure detecting element EM in a direction toward a prescribed one of the opposite ends of the array of elements E. More specifically described, the checking means 76 judges whether the pressing force HDP applied to the pressure-pulse-wave sensor 36 is appropriate, based on a time difference ΔT between a time when a prescribed periodic portion of the pressure pulse wave is detected by the highest-pressure detecting element EM, and a time when an identical periodic portion of the pressure pulse wave is detected by the comparison element EC. Here, the prescribed periodic portion of pressure pulse wave may be a rising point, a peak point (point "c" in FIG. 5), or a dicrotic notch (point "d" shown in FIG. 5). The rising point may be any of known rising points, such as a point (point "b" in FIG. 5) where the rate of increase of magnitude of the pulse wave takes a maximal value; a point where a differentiated waveform obtained by differentiating the pressure pulse wave takes a maximal value; or a point corresponding to one fifth of a pulse pressure of the pressure pulse wave. However, a minimal point (point "a" in FIG. 5) is not used as the rising point, because the minimal point is easily influenced by noise and accordingly a time of occurrence of the minimal point cannot be accurately determined.

Figure 7:
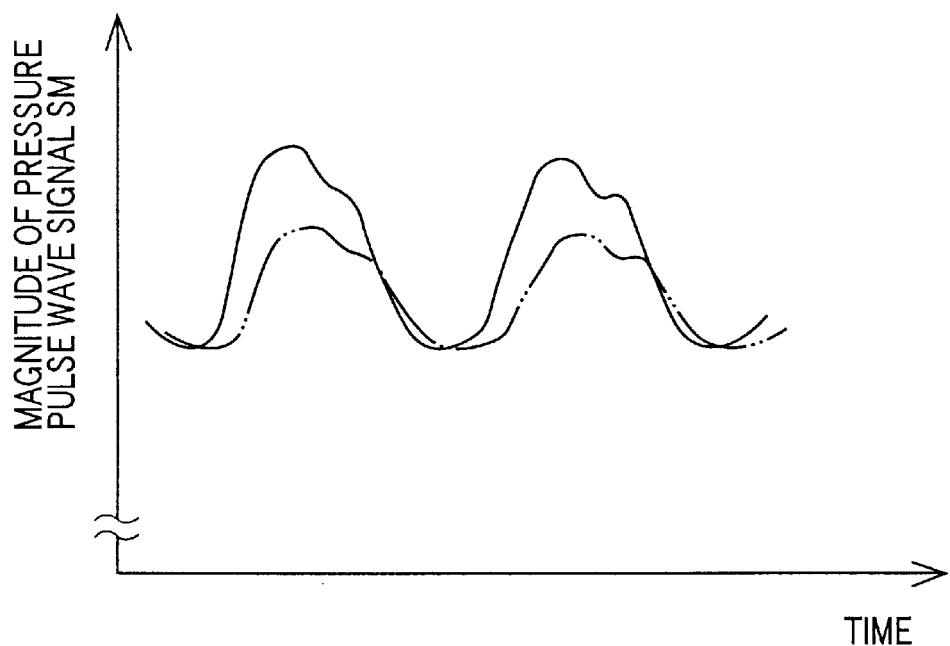
FIG. 7 is a graph showing a pressure pulse wave (indicated at solid line) detected by a highest-pressure detecting element EM of the pressure-pulse-wave sensor, and a pressure pulse wave (indicated at two-dot chain line) detected by a semiconductor pressure-sensing element E(x) of the sensor that is positioned right above a non-flattened portion of a wall of a carotid artery.
Figure 8:
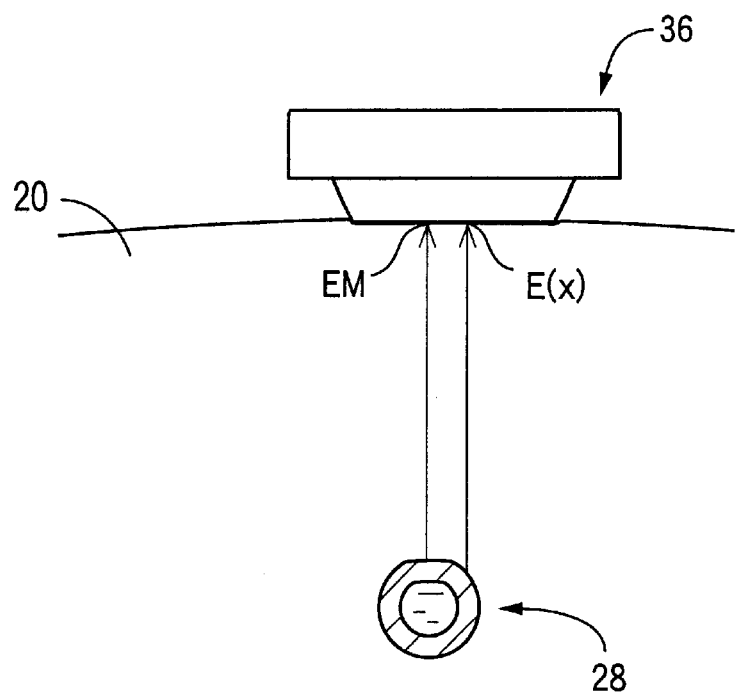
FIG. 8 is a view showing a relationship between respective positions of the highest-pressure detecting element EM and the semiconductor pressure-sensing element E(x), and the carotid artery.

Hereinafter, the reason why the above-indicated time difference ΔT is useful in judging whether the pressing force HDP applied to the pressure-pulse-wave sensor 36 is appropriate, will be explained. FIG. 7 shows a graph representing a pressure pulse wave (indicated at solid line) detected by the highest-pressure detecting element EM, and a pressure pulse wave (indicated at two-dot chain line) detected by a semiconductor pressure-sensing element E(x) positioned right above a portion of the wall of the carotid artery 28 that is not flattened. FIG. 8 shows a relationship between respective positions of the highest-pressure detecting element EM and the semiconductor pressure-sensing element E(x), and the carotid artery 28. As shown in FIG. 7, a phase of the pressure pulse wave detected by the semiconductor pressure-sensing element E(x) is later than that of the pressure pulse wave detected by the highest-pressure detecting element EM. This is because a flattened portion of the wall of the carotid artery 28 is not influenced by a visco-elasticity of the wall, but the non-flattened portion of the wall is influenced by the same. Thus, if the phase of the pressure pulse wave detected by the pressure-sensing element E(x) is not later than that of the pressure pulse wave detected by the highest-pressure detecting element EM, or if the former phase is later than the latter phase by a considerably short time only, it can said that the pressure-sensing element E(x) is positioned right above a flattened portion of the wall of the carotid artery 28 (that is, that a portion of the wall of the artery is flattened).

Therefore, if the time difference ΔT between the time when the prescribed periodic portion of the pressure pulse wave is detected by the highest-pressure detecting element EM, and the time when the identical periodic portion of the pressure pulse wave is detected by the comparison element EC is smaller than an upper-limit time TH1 that is experimentally determined in advance, it can be judged that a portion of the wall of the carotid artery 28 is flattened by the pressing of the pressure-pulse-wave sensor 36, that is, that the pressing force HDP applied to the sensor 36 is appropriate. A distance between the highest-pressure detecting element EM and the comparison element EC is prescribed such that the distance is shorter than the diameter of the carotid artery 28 (e.g., is equal to one fifth of the diameter).

A pulse-wave-propagation-velocity determining means 78 successively determines a time difference (i.e., a pulse-wave propagation time) DT (msec) between a time when a prescribed periodic portion of each of successive heartbeat-synchronous pulses of the heart-sound waveform represented by the heart-sound signal SH is detected and a time when a prescribed periodic portion of a corresponding one of successive heartbeat-synchronous pulses of the pressure pulse wave represented by the pressure-pulse-wave signal SM, based on the heart-sound signal SH continuously detected by the heart-sound microphone 12 and the pressure-pulse-wave signal SM continuously detected by the highest-pressure detecting element EM of the pressure-pulse-wave sensor 36, each signal SH, SM being detected in the state in which the pressing force HDP applied to the sensor 36 is held at the optimum pressing force HDPO by the pressing-force changing means 74. In addition, the means 78 successively determines a pulse-wave propagation velocity PWV (m/sec), i.e., a velocity at which a pulse wave propagates through an artery of the subject, based on the thus determined pulse-wave propagation time DT according to the following Expression 1, and operates the display device 58 to display the thus determined pulse-wave propagation velocity PWV. In Expression 1, "L" (m) indicates a distance from left ventricle via aorta to the position where the sensor 36 is worn, and a constant value that is experimentally determined in advance is employed as L.

$$PWV=L/DT \qquad \text{(Expression 1)}$$

Figure 9:
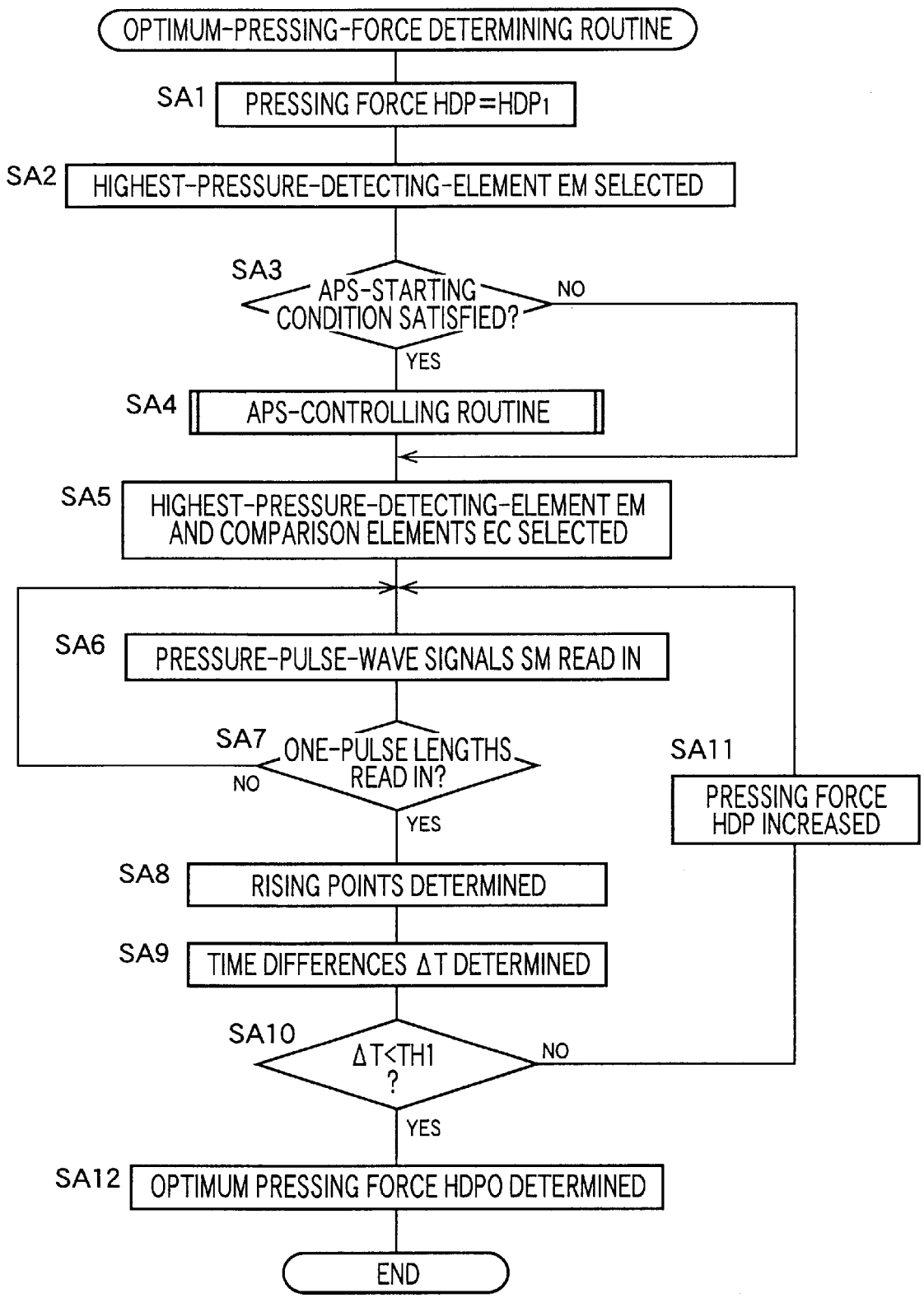
FIG. 9 is a flow chart representing an optimum-pressing-force determining routine according to which the control device shown in the block diagram of FIG. 6 is operated.
Figure 10:
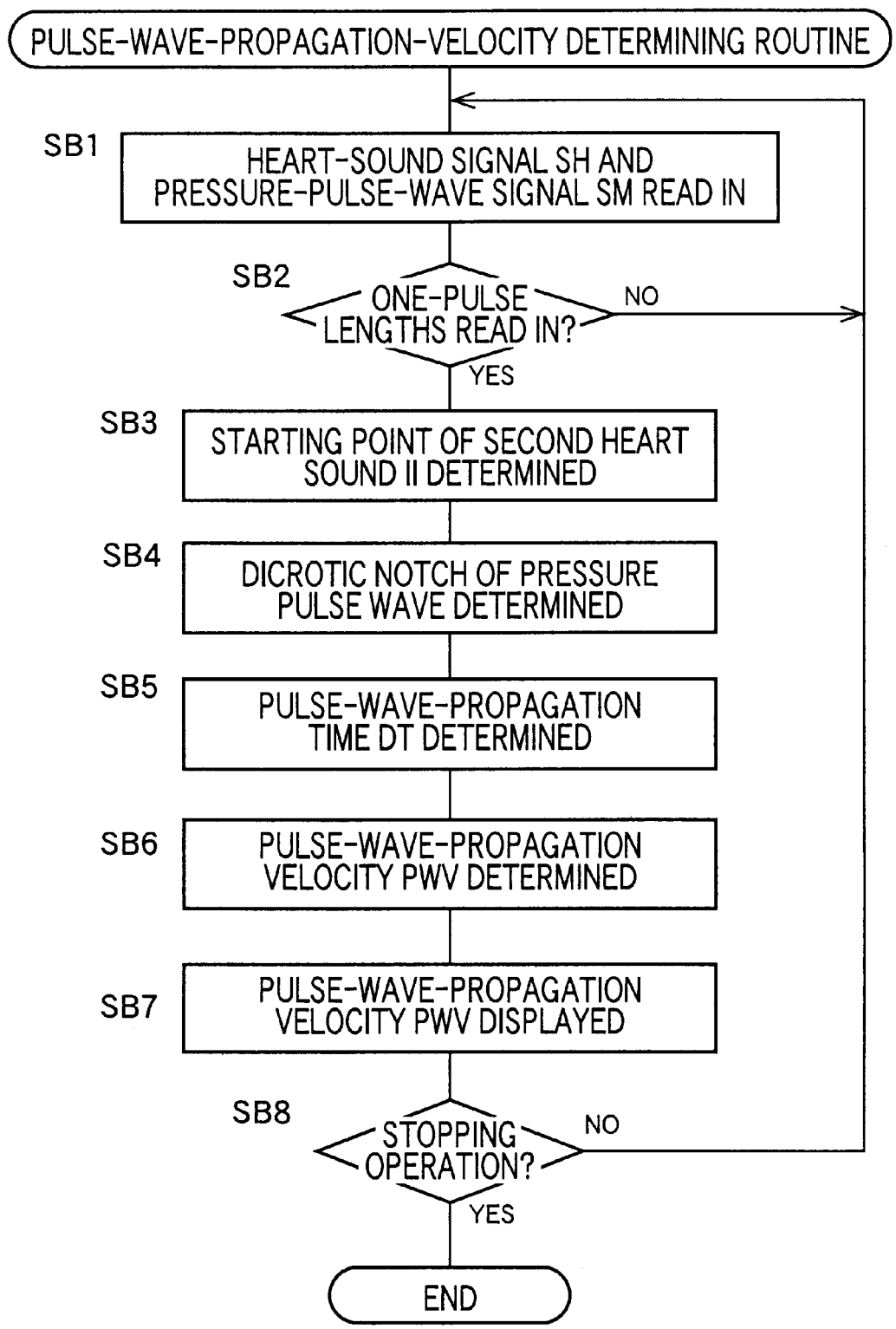
FIG. 10 is a flow chart representing a pulse-wave-propagation-velocity determining routine according to which the control device shown in the block diagram of FIG. 6 is operated.

FIGS. 9 and 10 are flow charts representing the control functions of the control device 18 shown in FIG. 6. FIG. 9 shows an optimum-pressing-force determining routine; and FIG. 10 shows a pulse-wave-propagation-velocity determining routine.

In FIG. 9, first, the control device 18 carries out Step SA1 (hereinafter, "Step" is omitted, if appropriate) corresponding to the pressing-force changing means 74. At SA1, the control device operates the pressing device 44 to change the pressure in the pressure chamber 38 so that the pressing force HDP applied to the pressure-pulse-wave sensor 36 is held at the prescribed first pressing force HDP1. The first pressing force HDP1 is sufficiently lower than a usual optimum pressing force HDPO, and is experimentally determined, in advance, at such a value which assures that the control device can accurately determine respective peak-point magnitudes of the respective pressure pulse waves represented by the respective pressure-pulse-wave signals SM supplied from the respective semiconductor pressure-sensing elements E.

Then, the control goes to SA2 corresponding to the highest-pressure-detecting-element selecting means 70. At SA2, the control device reads in one heartbeat-synchronous pulse of the pressure-pulse-wave signal SM supplied from each of the fifteen semiconductor pressure-sensing elements E, and determines a peak point of the pulse of the pressure-pulse-wave signal SM and a magnitude or height of the peak point of the pulse. In addition, the control device selects, as the highest-pressure detecting element EM, one of the elements E that supplies the signal SM having the greatest peak-point magnitude of the respective peak-point magnitudes of the respective signals SM supplied from the elements E.

Then, the control proceeds with SA3 and SA4 corresponding to the optimum-pressing-position determining means 72. At SA3, the control device judges whether the prescribed pressing-position changing condition (i.e., the APS-starting condition) is satisfied, i.e., whether the highest-pressure-detecting element EM is located in one of the prescribed opposite end portions of the array of elements E. If a negative judgment made at SA3, the control goes to SA5 and the following steps, described later.

On the other hand, if a positive judgment is made at SA3, that is, if the pressing position where the pressure-pulse-wave sensor 36 is pressed against the carotid artery 28 is not appropriate, the control proceeds with SA4, i.e., an APS-controlling routine. According to this APS-controlling routine, the control device 18 determines the optimum pressing position where the highest-pressure-detecting element EM is located at substantially the middle of the array of elements E. To this end, the control device operates the pressing device 44 and the widthwise-direction moving device 46 to once move the pressure-pulse-wave sensor 36 away from the body surface 32, move the pressing device 44 and the sensor 36 over a prescribed distance, and again press the sensor 36 with the prescribed pressing force HDP1. In this state, the control device again judges whether the highest-pressure-detecting element EM is located at substantially the middle of the array of elements E. SA3 and SA4 are repeated till a positive judgment is made.

Thus, the control device positions, at SA4, the pressure-pulse-wave sensor 36 at the optimum pressing position. Then, the control goes to SA5 corresponding to the highest-pressure-detecting-element selecting means 70. At SA5, the control device selects a new highest-pressure detecting element EM, in the same manner as that described in connection with SA2, and additionally selects, as two comparison elements EC, respective semiconductor pressure-sensing elements E located on both sides of, and next to, the new highest-pressure detecting element EM.

Then, the control goes to SA6 to SA10 corresponding to the pressing-force checking means 76. First, at SA6, the control device periodically reads in, at a prescribed sampling period Ts, the respective pressure-pulse-wave signals SM supplied from the semiconductor pressure-sensing elements E and, then at SA7, the control device judges whether the control device has read in one heartbeat-synchronous pulse of each of the pressure-pulse-wave signals SM at SA6. If a negative judgment is made at SA7, SA6 and the following steps are repeated. Meanwhile, if a positive judgment is made at SA7, the control goes to SA8 where the control device determines, as a rising point, a point where the rate of increase of magnitude of the one pulse of the pressure pulse wave represented by the pressure-pulse-wave signal SM supplied from the highest-pressure detecting element EM during the repetition of SA6 and SA7 takes a maximal value, and additionally determines, as a standard time Tst, a time of occurrence of the rising point. Similarly, the control device determines a rising point of the one pulse of each of the respective pressure-pulse-wave signals SM supplied from the two comparison elements EC selected at SA5, and determines, as a comparison time Tco, a time of occurrence of each of the two rising points.

Then, at SA9, the control device determines a time difference ΔT between the standard time Tst and each of the two comparison times Tco, all determined at SA8. This time difference ΔT is calculated as an absolute value. Subsequently, at SA10, the control device judges whether each one of the two time differences ΔT determined at SA9 is smaller than the prescribed upper-limit time TH1 of from the sampling period Ts to three times the period Ts. It is preferred that the control device make a positive judgment at SA10, if both of the two time differences ΔT are judged as being smaller than the upper-limit time TH1. However, the control device may be so modified as to make a positive judgment at SA10, if at least one of the two time differences ΔT is judged as being smaller than the upper-limit time TH1.

If a negative judgment is made at SA10, the control goes to SA11 corresponding to the pressing-force changing means 74. At SA11, the control device operates the pressing device 44 to increase, by a prescribed increment amount, the pressing force HDP applied to the pressure-pulse-wave sensor 36, and then the control goes back to SA6 and the following steps. Meanwhile, if a positive judgment is made at SA10, the control goes to SA12 to determine, as the optimum pressing force HDPO, the pressing force HDP applied to the pressure-pulse-wave sensor 36 at that time.

Then, the control device carries out the pulse-wave-propagation-velocity determining routine of FIG. 10. First, at SB1, the control device reads in the heart-sound signal SH supplied from the heart-sound microphone 12 and the pressure-pulse-wave signal SM supplied from the highest-pressure detecting element EM of the pressure-pulse-wave sensor 36.

Subsequently, at SB2, the control device judges whether the control device has read in one heartbeat-synchronous pulse of each of the heart-sound signal SH and the pressure-pulse-wave signal SM, by judging, e.g., whether the control device has read in a rising point of the one pulse of the pressure-pulse-wave signal SM. If a negative judgment is made at SB2, the control goes back to SB1 to continue reading in the heart-sound signal SH and the pressure-pulse-wave signal SM.

Meanwhile, if a positive judgment is made at SB2, the control goes to SB3 to determine a time of detection of a starting point of a second heart sound II, based on the heart-sound signal SH read in at SB1. Then, at SB4, the control device determines a time of detection of a dicrotic notch of the carotid pulse wave, based on the pressure-pulse-wave signal SM read in at SB1. Both the second heart sound II and the dicrotic notch occur when the aortic valve closes. Therefore, the dicrotic notch of the carotid pulse wave provides a prescribed periodic portion corresponding to the second heart sound II.

Figure 11:
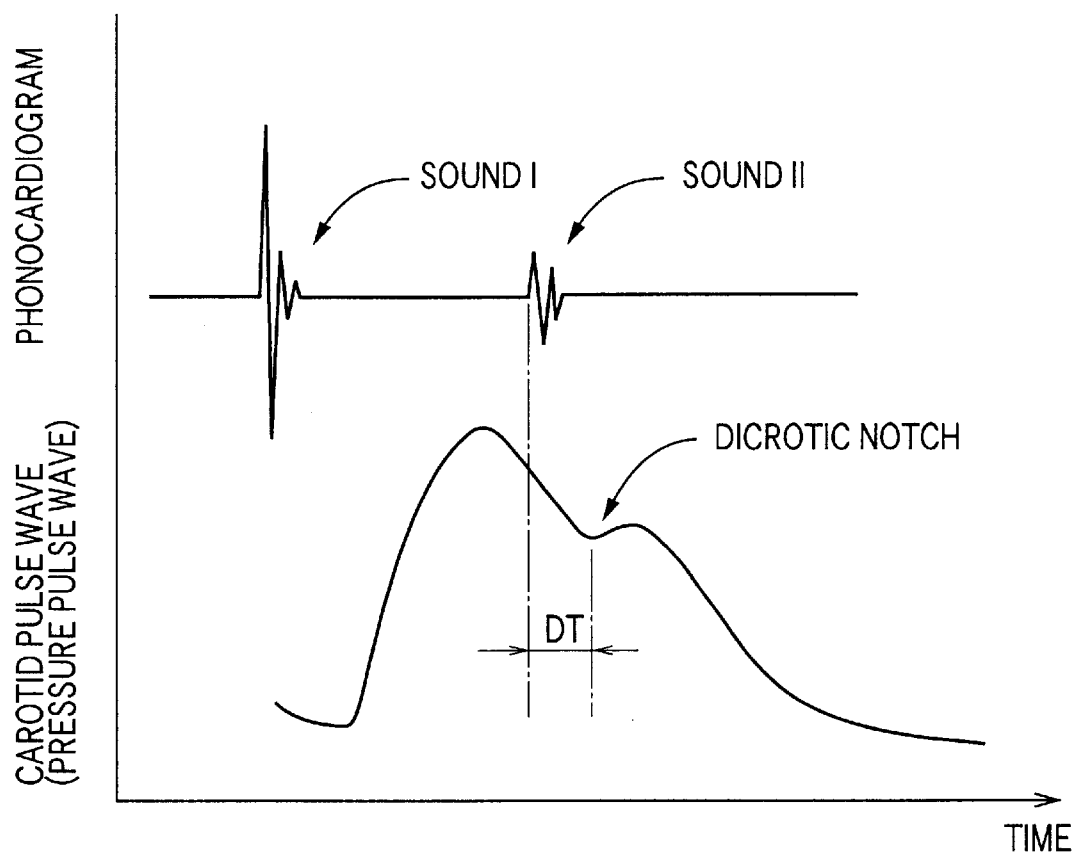
FIG. 11 is a graph showing an example of a pulse-wave propagation time DT that is determined at Step SB5 of FIG. 10.

At SB5, the control device determines, as a pulse-wave propagation time DT, a time difference between the time of detection of the starting point of the second heart sound II determined at SB3 and the time of detection of the notch determined at SB4. FIG. 11 illustrates the pulse-wave propagation time DT determined at SB5.

Subsequently, at SB6, the control device determines, according to Expression 1, a pulse-wave propagation velocity PWV based on the pulse-wave propagation time DT determined at SB5, and operates, at SB9, the display device 58 to display the thus determined pulse-wave propagation velocity PWV.

Then, at SB8, the control device judges whether a stop button, not shown, has been operated by the operator and accordingly the control device has received a stop signal supplied from the stop button. If a negative judgment is made at SB8, the control goes back to SB1 and the following steps to continue successively measuring pulse-wave propagation velocities PWV. Meanwhile, if a positive judgment is made at SB8, the present routine is ended.

As is apparent from the foregoing description of the illustrated embodiment, at SA6 to SA10 (the pressing-force checking means 76), the control device judges whether the pressing force HDP applied to the pressure-pulse-wave sensor 36 is appropriate, based on the time difference ΔT between the time when the rising point of the pressure pulse wave is detected by the highest-pressure detecting element EM and the time when the rising point of the pressure pulse wave is detected by each of the two comparison elements EC located next to the element EM. Thus, the control device can determine an appropriate pressing force applied to the sensor 36 to flatten a portion of the wall of the carotid artery 28, without needing to flatten the entirety of the arterial wall.

Next, there will be described another embodiment of the present invention. The same reference numerals as used in the above-described embodiment are used to designate the corresponding elements of the present embodiment, and the description thereof is omitted.

Figure 12:
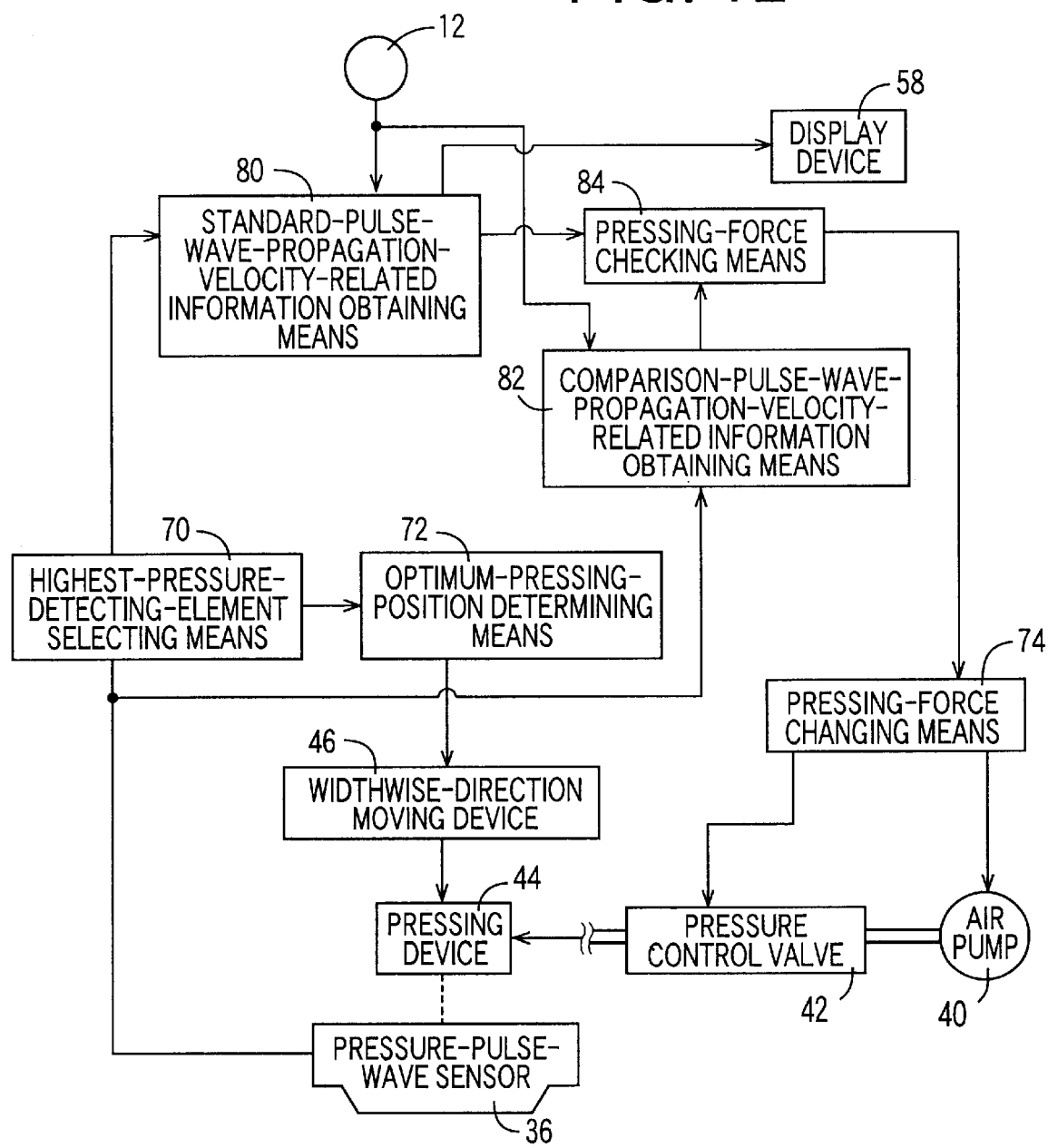
FIG. 12 is a block diagram corresponding to FIG. 6, for explaining essential functions of a control device of another pulse-wave-propagation-velocity measuring apparatus as a second embodiment of the present invention.

The present invention differs from the above-described embodiment with respect to only control functions of a control device 18 that relate to the function of judging whether a pressing force applied to a pressure-pulse-wave sensor 36 is appropriate. FIG. 12 shows a block diagram for explaining essential control functions of the control device 18.

A standard-pulse-wave-propagation-velocity-related-information obtaining means 80 successively determines, as a standard pulse-wave propagation time DTst, a time difference (i.e., a pulse-wave propagation time) DT (msec) between a time when a prescribed periodic portion of each of successive heartbeat-synchronous pulses of the heart-sound waveform represented by the heart-sound signal SH is detected and a time when a prescribed periodic portion of a corresponding one of successive heartbeat-synchronous pulses of the pressure pulse wave represented by the pressure-pulse-wave signal SM, based on the heart-sound signal SH continuously detected by the heart-sound microphone 12 and the pressure-pulse-wave signal SM continuously detected by the highest-pressure detecting element EM of the pressure-pulse-wave sensor 36. In addition, the means 80 successively determines, as a standard pulse-wave propagation velocity PWVst, a pulse-wave propagation velocity PWV (m/sec) based on the thus determined standard pulse-wave propagation time DTst according to the above-explained Expression 1. The meaning of the prescribed portion of the heart-sound waveform is the same as that described in connection with the previously-described embodiment.

A comparison-pulse-wave-propagation-velocity-related-information obtaining means 82 successively determines, as a comparison pulse-wave propagation time DTco, a pulse-wave propagation time DT in basically the same manner as that described in connection with the standard-pulse-wave-propagation-velocity-related-information obtaining means 80, however, based on the pressure-pulse-wave signal SM continuously detected by the semiconductor pressure-sensing element E (i.e., the comparison element EC) distant by the prescribed distance from the highest-pressure detecting element EM in the direction toward the prescribed one end of the array of elements. In addition, the means 82 successively determines, as a comparison pulse-wave propagation velocity PWVco, a pulse-wave propagation velocity PWV (m/sec) based on the thus determined comparison pulse-wave propagation time DTco according to Expression 1.

A pressing-force checking means 84 first determines a comparison value by comparing the standard pulse-wave-propagation-velocity-related information (i.e., the standard pulse-wave propagation time DTst or the standard pulse-wave propagation velocity PWVst) obtained by the means 80 and the comparison pulse-wave-propagation-velocity-related information (i.e., the comparison pulse-wave propagation time DTco or the comparison pulse-wave propagation velocity PWVco) obtained by the means 82. Then, based on the thus determined comparison value, the means 84 judges whether the pressing force applied by the pressing device 44 to the pressure-pulse-wave sensor 36 is appropriate. The comparison value is defined as a value which indicates a degree of difference between the standard pulsewave-propagation-velocity-related information and the comparison pulse-wave-propagation-velocity-related information, and may be a difference between the two sorts of information or a ratio of one of the two sorts of information to the other sort of information.

As described in connection with the previous embodiment, if the pressing force HDP applied to the pressure-pulse-wave sensor 36 is appropriate, respective phases of the respective pressure pulse waves detected by the highest-pressure detecting element EM and the comparison element EC substantially coincide with each other. That is, a time when the prescribed portion of the pressure pulse wave is detected by the highest-pressure detecting element EM and a time when the prescribed portion of the pressure pulse wave is detected by the comparison element EC substantially coincide with each other. Therefore, if the pressing force HDP applied to the pressure-pulse-wave sensor 36 is appropriate, then the standard pulse-wave propagation time DTst and the comparison pulse-wave propagation time DTco should be substantially equal to each other. Since pulse-wave propagation velocity PWV corresponds, one to one, to pulse-wave propagation time DT according to Expression 1, if the standard pulse-wave propagation time DTst and the comparison pulse-wave propagation time DTco are substantially equal to each other, then the standard pulse-wave propagation velocity PWVst and the comparison pulse-wave propagation velocity PWVco should be substantially equal to each other. Thus, if the above-explained comparison value falls within a reference range that is experimentally determined in advance, then the pressing-force checking means 84 judges that the pressing force HDP applied to the pressure-pulse-wave sensor 36 is appropriate. This reference range may be a considerably narrow range whose middle value is equal to either zero if the comparison value is a difference, or to one if the comparison value is a ratio.

Figure 13:
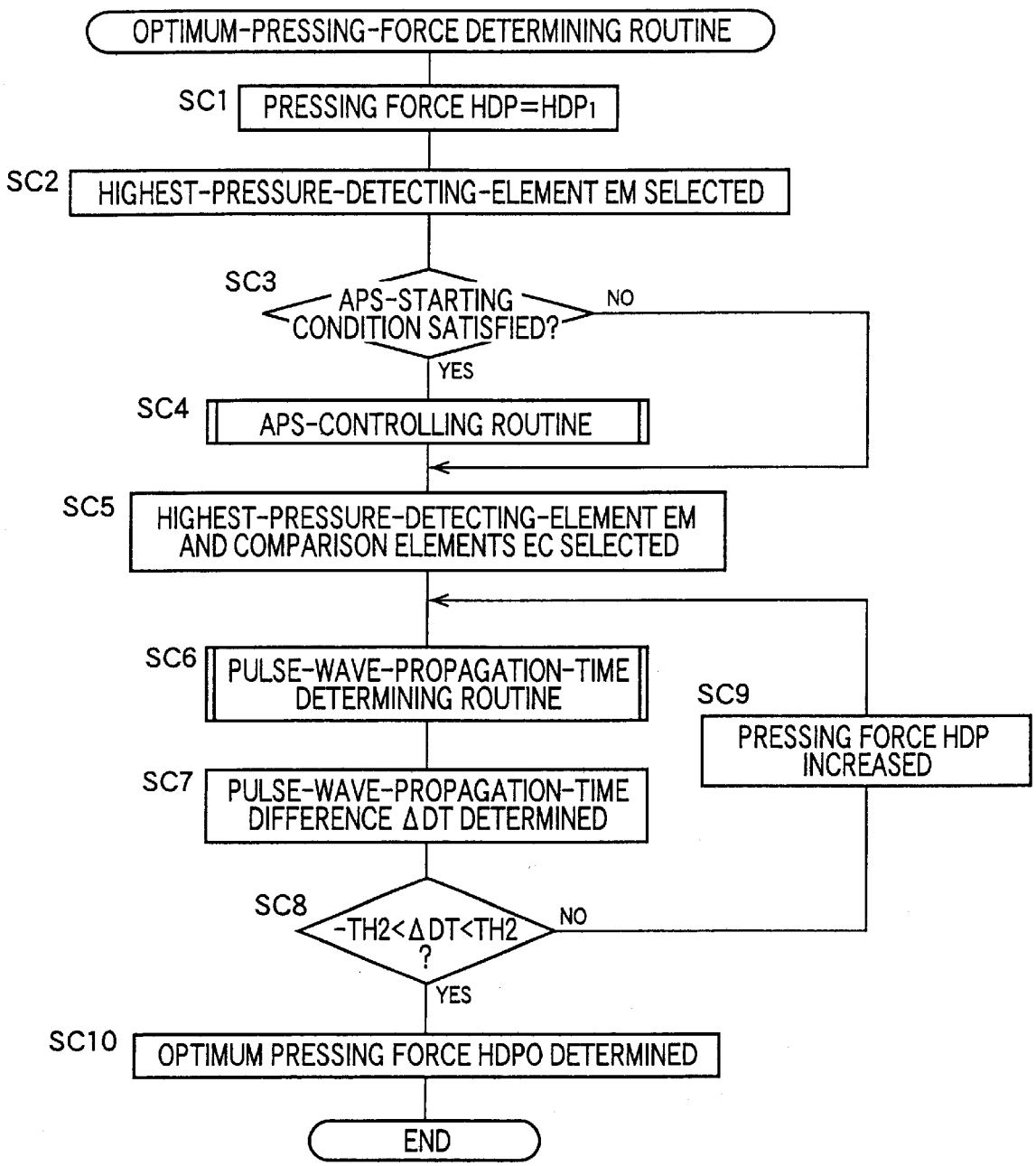
FIG. 13 is a flow chart representing an optimum-pressing-force determining routine according to which the control device shown in the block diagram of FIG. 12 is operated.

FIG. 13 shows a flow chart representing an optimum-pressing-force determining routine corresponding to the control functions of the control device 18, shown in FIG. 12.

First, the control device carries out SC1 to SC5 that are identical with SA1 to SA5 of FIG. 9, that is, the control device determines a pressing position where the pressure-pulse-wave sensor 36 is pressed against the carotid artery 28, and selects a highest-pressure detecting element EM, and a comparison element EC.

Then, the control goes to SC6, i.e., a pulse-wave-propagation-time determining routine corresponding to the standard-pulse-wave-propagation-velocity-related-information obtaining means 80 and the comparison-pulse-wave-propagation-velocity-related-information obtaining means 82. According to the pulse-wave-propagation-time determining routine, the control device determines a pulse-wave propagation time DT in the same manner as SB1 to SB5 of the pulse-wave-propagation-velocity determining routine of FIG. 10, based on the pressure pulse wave supplied from each of the highest-pressure detecting element EM and the comparison element EC, both determined at SC5. More specifically described, the control device determines a standard pulse-wave propagation time DTst based on the pressure-pulse-wave signal SM supplied from the highest-pressure detecting element EM, and determines a comparison pulse-wave propagation time DTco based on the pressure-pulse-wave signal SM supplied from the comparison element EC.

Then, the control goes to SC7 and SC8 corresponding to the pressing-force checking means 84. First, at SC7, the control device determines a pulse-wave-propagation-time difference Δ DT between the standard pulse-wave propagation time DTst and the comparison pulse-wave propagation time DTco, both determined at SC6.

Next, at SC8, the control device judges whether the pulse-wave-propagation-time difference Δ DT determined at SC7 falls within the prescribed reference range, i.e., whether the difference Δ DT is greater than a lower-limit value, −TH2, of the reference range, and smaller than an upper-limit value, TH2, of the reference range. If a negative judgment is made at SC8, the control goes to SC9 that is identical with SA11 of FIG. 9 and then the control device repeats SC6 and the following steps.

On the other hand, if a positive judgment is made at SC8, the control goes to SC10 to determine, as an optimum pressing force HDPO, a pressing force HDP applied to the pressure-pulse-wave sensor 36 at that time. After SC10, the control device carries out the pulse-wave-propagation-velocity determining routine of FIG. 10.

As is apparent from the foregoing description of the second embodiment in which the flow chart of FIG. 13 is employed, at SC6 (the standard-pulse-wave-propagation-velocity-related-information obtaining means 80 and the comparison-pulse-wave-propagation-velocity-related-information obtaining means 82), the control device determines the standard pulse-wave propagation time DTst based on the heart-sound signal SH detected by the heart-sound microphone 12 and the pressure pulse wave detected by the highest-pressure detecting element EM, and additionally determines the comparison pulse-wave propagation time DTco based on the heart-sound signal SH detected by the heart-sound microphone 12 and the pressure pulse wave detected by the comparison element EC. Since each of the standard pulse-wave propagation time DTst and the comparison pulse-wave propagation time DTco is determined based on the time of occurrence of the starting point of the second heart sound II as one of the two reference points, the difference between the two times DTst, DTco results from the difference between the time when the dicrotic notch of the pressure pulse wave is detected by the highest-pressure detecting element EM and the time when the same is detected by the comparison element EC. Thus, at SC7 and SC8 (the pressing-force judging means 84), the control device can judge whether the pressing force HDP applied to the pressure-pulse-wave sensor 36 is appropriate, based on the pulse-wave-propagation-time difference A DT between the two time DTst, DTco. Thus, the control device can determine the optimum pressing force HDPO, without needing to flatten the entirety of the carotid arterial 28.

Figure 14:
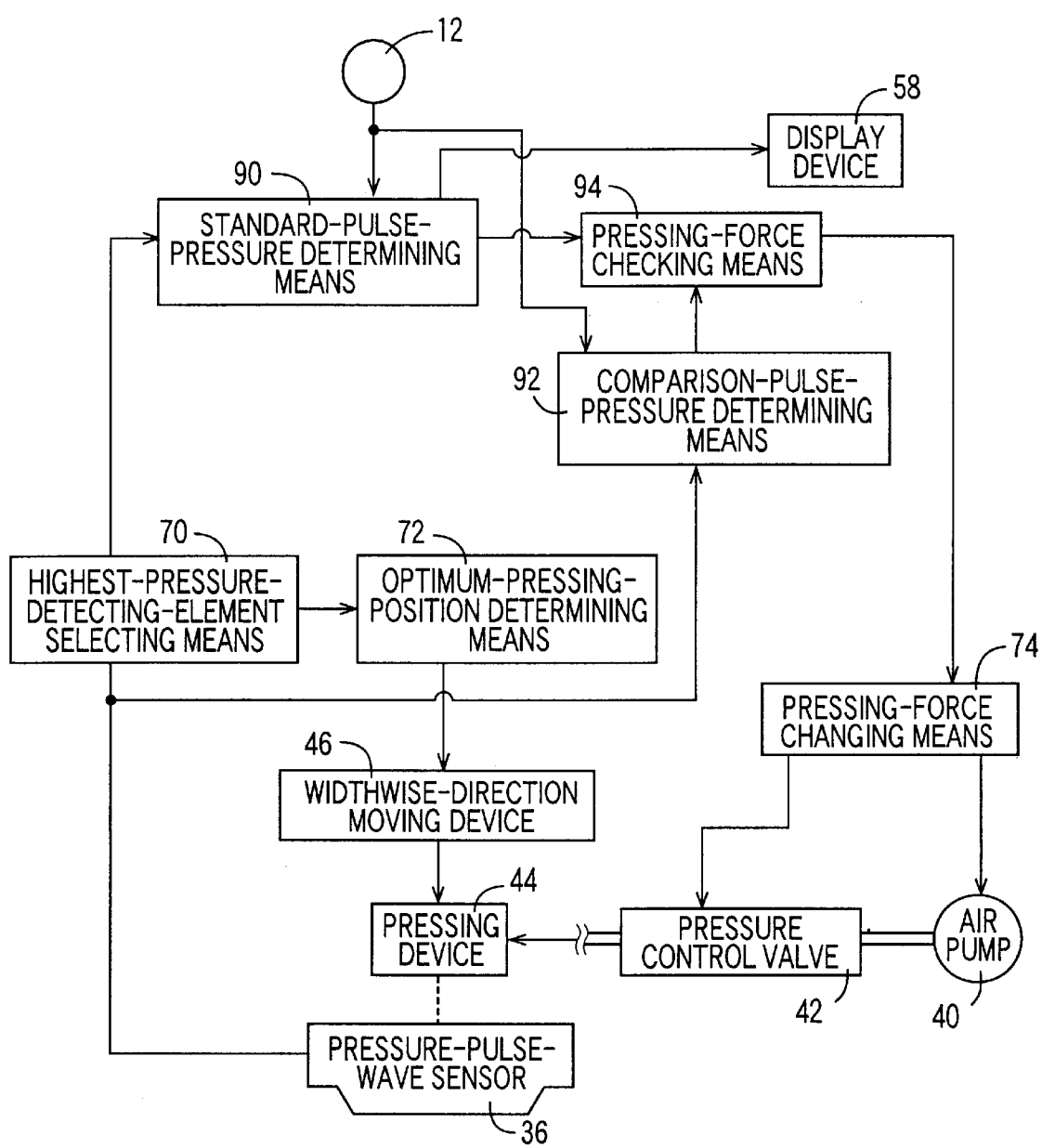
FIG. 14 is a block diagram corresponding to FIG. 6, for explaining essential functions of a control device of another pulse-wave-propagation-velocity measuring apparatus as a third embodiment of the present invention.

Next, there will be described yet another embodiment of the present invention that is different from the above-described two embodiments. The present invention differs from the first embodiment with respect to only control functions of a control device 18 that relate to the function of judging whether a pressing force applied to a pressure-pulse-wave sensor 36 is appropriate. FIG. 14 shows a block diagram for explaining essential control functions of the control device 18.

Figure 5:
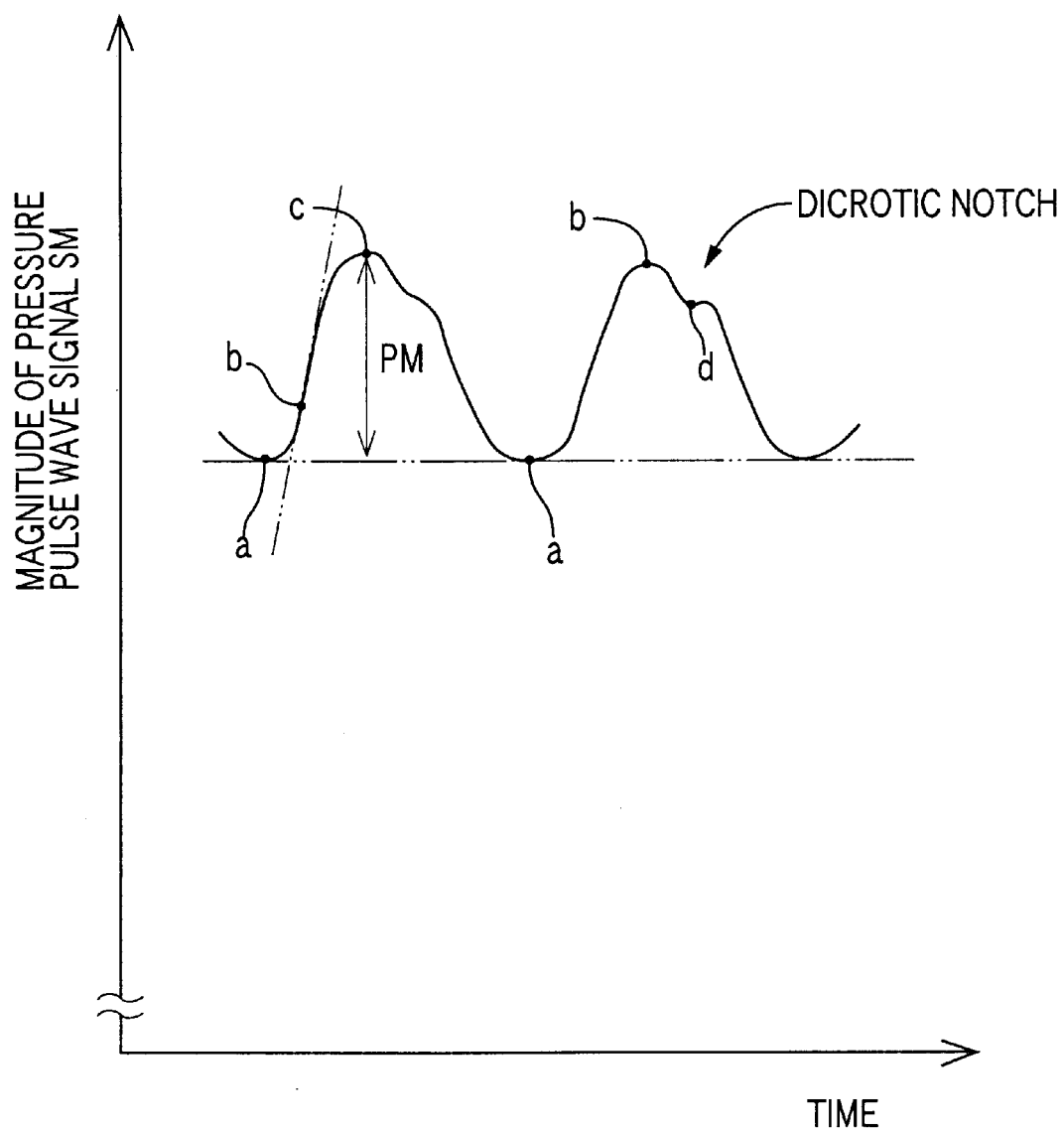
FIG. 5 is a graph showing an example of a pressure pulse wave represented by a pressure-pulse-wave signal SM supplied from a pressure-sensing element of the pressure-pulse-wave sensor of FIG. 1.

A standard-pulse-pressure determining means 90 determines, as a standard pulse pressure PMst, a pulse pressure PM of the pressure pulse wave represented by the pressure-pulse-wave signal SM detected by the highest-pressure detecting element EM of the pressure-pulse-wave sensor 36. Here, the pulse pressure PM is defined, as illustrated in FIG. 5, a difference between a maximal pressure and a minimal pressure of one heartbeat-synchronous pulse of the pressure pulse wave.

A comparison-pulse-pressure determining means 92 determines, as a comparison pulse pressure PMco, a pulse pressure PM of the pressure pulse wave represented by the pressure-pulse-wave signal SM detected by the semiconductor pressure-sensing element E (i.e., the comparison element EC) distant by the prescribed distance from the highest-pressure detecting element EM in the direction toward the prescribed one end of the array of elements.

A pressing-force checking means 94 first determines a comparison value by comparing the standard pulse pressure PMst determined by the means 90 and the comparison pulse pressure PMco determined by the means 92. Then, based on the thus determined comparison value, the means 94 judges whether the pressing force applied by the pressing device 44 to the pressure-pulse-wave sensor 36 is appropriate. The comparison value is defined as a value which indicates a degree of difference between the standard pulse pressure PMst and the comparison pulse pressure PMco, and may be a difference between the two pulse pressures PMst, PMco, or a ratio of one of the two pulse pressures to the other pulse pressure.

As shown in FIG. 7, the pulse pressure PM of the pressure pulse wave (indicated at two-dot chain line) detected by the semiconductor pressure-sensing element E(x) positioned right above the non-flattened portion of the wall of the carotid artery 28 is smaller than that PM of the pressure pulse wave (indicated at solid line) detected by the highest-pressure detecting element EM positioned right above the flattened portion of the arterial wall. The reason for this is that the greater pressure loss resulting from the viscoelasticity of the arterial wall occurs to the non-flattened portion than to the flattened portion. Thus, if the pulse pressure PM of the pressure pulse wave detected by the comparison element EC is substantially equal to that PM of the pressure pulse wave detected by the highest-pressure detecting element EM, then it can judged that the comparison element EC is positioned right above a flattened portion of the arterial wall (i.e., that a portion of the arterial wall is flattened).

Thus, if the above-explained comparison value falls within a reference range that is experimentally determined in advance, then the pressing-force checking means 94 judges that the pressing force HDP applied to the pressure-pulse-wave sensor 36 is appropriate. This reference range may be a considerably narrow range whose middle value is equal to either zero if the comparison value is a difference, or to one if the comparison value is a ratio.

Figure 15:
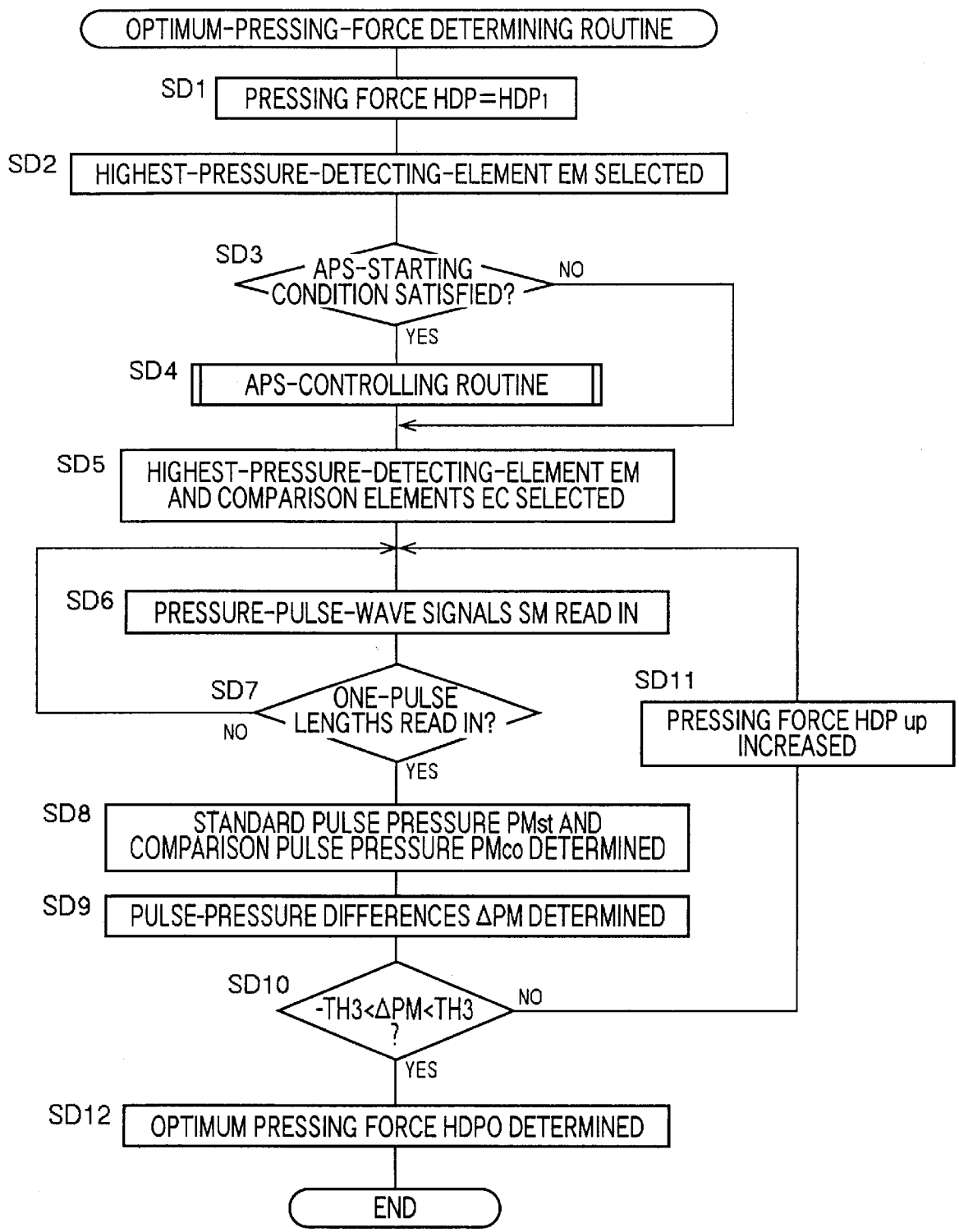
FIG. 15 is a flow chart representing an optimum-pressing-force determining routine according to which the control device shown in the block diagram of FIG. 14 is operated.

FIG. 15 shows a flow chart representing an optimum-pressing-force determining routine corresponding to the control functions of the control device 18, shown in FIG. 14.

First, the control device carries out SD1 to SD7 that are identical with SA1 to SA7 of FIG. 9, that is, the control device determines a pressing position where the pressure-pulse-wave sensor 36 is pressed against the carotid artery 28, selects a highest-pressure detecting element EM, and a comparison element EC, and reads in one heartbeat-synchronous pulse of each of the respective pressure-pulse-wave signals SM supplied from the sensor 36.

Then, the control goes to SD8, i.e., the standard-pulse-pressure determining means 90 and the comparison-pulsepressure determining means 92. At SD8, the control device determines, as a standard pulse pressure PMst, a pulse pressure PM of the pressure pulse wave represented by the pressure-pulse-wave signal SM supplied from the highest-pressure detecting element EM while SD6 and SD7 are repeated, and determines, as a comparison pulse pressure PMco, a pulse pressure PM of the pressure pulse wave represented by the pressure-pulse-wave signal SM supplied from the comparison element EC while SD6 and SD7 are repeated.

Then, the control goes to SD9 and SD10 corresponding to the pressing-pressure checking means 94. First, at SD9, the control device determines a pulse-pressure difference Δ PM between the standard pulse pressure PMst and the comparison pulse pressure PMco, both determined at SD8.

Next, at SD10, the control device judges whether the pulse-pressure difference Δ PM determined at SD9 falls within a prescribed reference range, i.e., whether the pulse-pressure difference ΔPM is greater than a lower-limit value, −TH3, of the reference range, and smaller than an upper-limit value, TH3, of the reference range. If a negative judgment is made at SD10, the control goes to SD11 that is identical with SA11 of FIG. 9 and then the control device repeats SD6 and the following steps.

On the other hand, if a positive judgment is made at SD10, the control goes to SD12 to determine, as an optimum pressing force HDPO, a pressing force HDP applied to the pressure-pulse-wave sensor 36 at that time. After SD12, the control device carries out the pulse-wave-propagation-velocity determining routine of FIG. 10.

As is apparent from the foregoing description of the third embodiment in which the flow chart of FIG. 15 is employed, at SD8 (the standard-pulse-pressure determining means 90 and the comparison-pulse-pressure determining means 92), the control device determines, as the standard pulse pressure PMst, the pulse pressure PM of the pressure pulse wave detected by the highest-pressure detecting element EM, and additionally determines, as the comparison pulse pressure PMco, the pulse pressure PM of the pressure pulse wave detected by the comparison element EC. An event that the standard pulse pressure PMst and the comparison pulse pressure PMco are substantially equal to each other indicates that a portion of the wall of the carotid artery 28 is flattened. Thus, at SD9 and SD10 (the pressing-force judging means 94), the control device can judge whether the pressing force HDP applied to the pressure-pulse-wave sensor 36 is appropriate, based on the pulse-pressure difference Δ PM between the two pulse pressures PMst, PMco. Thus, the control device can determine the optimum pressing force HDPO, without needing to flatten the entirety of the arterial 28.

While the present invention has been described in its embodiments by reference to the drawings, it is to be understood that the invention may otherwise be embodied.

For example, in each of the illustrated embodiments, the pressure-pulse-wave sensor 36 is adapted to be worn on the neck 20. However, it is possible to employ a pressure-pulse-wave sensor that is adapted to be worn on a different portion of the subject, such as a femoral portion.

In each of the illustrated embodiments, the heart-sound microphone 12 is employed as the heartbeat-synchronous-signal detecting device. However, a waveform (e.g., R-wave) of an electrocardiogram or a pulse wave is also a heartbeat-synchronous signal. Therefore, an electrocardiograph that includes a plurality of electrodes adapted to be worn on prescribed portions of a living subject and detects, through the electrodes, a waveform of an electrocardiogram, or a pulse-wave sensor, such as a photoelectric-pulse-wave that is adapted to be worn on an end portion of a finger to detect a pulse wave, may be employed as the heartbeat-synchronous-signal detecting device.

In each of the illustrated embodiments, the heart-sound microphone 12 is employed as the heartbeat-synchronous-signal detecting device, and accordingly the heartbeat-synchronous-signal detecting device is adapted to be worn on an upstream side of the pressure-pulse-wave sensor 36. However, the heartbeat-synchronous-signal detecting device may be adapted to be worn on a downstream side of the sensor 36.

The present invention may be embodied with various changes without departing from the spirit of the invention.

What is claimed is:

1. An apparatus for detecting a pressure pulse wave produced by an artery of a living subject, comprising:
   a pressure-pulse-wave sensor which has a pressing surface, and a plurality of pressure-detecting elements that are adapted to be arranged, in the pressing surface, in an array in a widthwise direction of the artery;
   a pressing device which adapted to press, with a pressing force, the pressure-pulse-wave sensor against the artery via a skin of the subject, so that each of the pressure-detecting elements detects the pressure pulse wave produced by the artery;
   a highest-pressure-detecting-element selecting means for selecting, as a highest-pressure-detecting element, a first one of the pressure-detecting elements that detects a highest one of respective pressures corresponding to the respective pressure pulse waves detected by the pressure-detecting elements; and
   a pressing-force checking means for judging whether the pressing force of the pressing device applied to the pressure-pulse-wave sensor is appropriate, based on a time difference between a first time when a prescribed portion of the pressure pulse wave is detected by the highest-pressure-detecting element and a second time when the prescribed portion of the pressure pulse wave is detected by a second one of the pressure-detecting elements that is distant by a prescribed distance from the highest-pressure-detecting element in a direction toward one of opposite ends of the array of pressure-detecting elements.

2. An apparatus according to claim 1, wherein each of the pressure-detecting elements comprises a semiconductor pressure-sensing element.

3. An apparatus according to claim 1, wherein the pressing device comprises:
   an elastic diaphragm which supports the pressure-pulse-wave sensor and which at least partly defines a pressure chamber;
   a pressurized-fluid supplying device which supplies, and discharges, a pressurized fluid to, and from, the pressure chamber; and
   a pressure changing means for operating the pressurized-fluid supplying device to change a pressure of the fluid present in the pressure chamber, and thereby changing the pressing force applied to the pressure-pulse-wave sensor.

4. An apparatus according to claim 1, further comprising a moving and positioning device which is adapted to move the pressure-pulse-wave sensor relative to the artery in the widthwise direction of the artery and thereby is adapted to position the pressure-pulse-wave sensor relative to the artery such that the array of pressure-detecting elements crosses over the artery in the widthwise direction of the artery.

5. An apparatus according to claim 1, further comprising:
- a heartbeat-synchronous-signal detecting device which detects a heartbeat-synchronous signal that is produced by the subject in synchronism with a heartbeat of the subject; and
- a pulse-wave-propagation-velocity-related-information obtaining means for obtaining pulse-wave-propagation-velocity-related information that is related to a velocity at which the pressure pulse wave propagates through the artery, based on the pressure pulse wave detected by the pressure-pulse-wave sensor and the heartbeat-synchronous signal detected by the heartbeat-synchronous-signal detecting device.

6. An apparatus according to claim 5, further comprising a display device which displays the pulse-wave-propagation-velocity-related information obtained by the pulse-wave-propagation-velocity-related-information obtaining means.

* * * * *

UNITED STATES PATENT AND TRADEMARK OFFICE
CERTIFICATE OF CORRECTION

PATENT NO. : 6,740,043 B2
DATED : May 25, 2004
INVENTOR(S) : Kiyoyuki Narimatsu

It is certified that error appears in the above-identified patent and that said Letters Patent is hereby corrected as shown below:

Title page,
Item [56], References Cited, U.S. PATENT DOCUMENTS, insert:

-- 5,119,822    06/1992    Niwa --
FOREIGN PATENT DOCUMENTS, insert:

-- EP    1 106 139 A1    06/2001
  JP    6-114018    04/1994
  JP    1-285244    11/1989 --

Signed and Sealed this

Twenty-eighth Day of September, 2004

JON W. DUDAS
*Director of the United States Patent and Trademark Office*